(12) United States Patent
Suzuki et al.

(10) Patent No.: US 8,482,796 B2
(45) Date of Patent: Jul. 9, 2013

(54) COLOR PROCESSING APPARATUS AND COLOR PROCESSING METHOD

(75) Inventors: Takahiro Suzuki, Tokyo (JP); Yoshitaka Sasaki, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 415 days.

(21) Appl. No.: 12/909,618

(22) Filed: Oct. 21, 2010

(65) Prior Publication Data

US 2011/0095203 A1    Apr. 28, 2011

(30) Foreign Application Priority Data

Oct. 27, 2009  (WO) .................. PCT/JP2009/068437

(51) Int. Cl.
   *H04N 1/60*    (2006.01)
(52) U.S. Cl.
   USPC ........................... 358/1.9; 702/189; 356/402
(58) Field of Classification Search
   USPC ............ 382/167; 702/189; 358/1.9; 356/300, 356/402
   See application file for complete search history.

(56) References Cited

U.S. PATENT DOCUMENTS

| | | | |
|---|---|---|---|
| 7,502,099 B2 | 3/2009 | Imura | |
| 2002/0012461 A1* | 1/2002 | MacKinnon et al. | 382/167 |
| 2002/0135768 A1* | 9/2002 | Sugiyama et al. | 356/405 |
| 2006/0092444 A1 | 5/2006 | Nakamura et al. | |
| 2006/0227319 A1 | 10/2006 | Imura | |
| 2007/0086009 A1* | 4/2007 | Ehbets et al. | 356/402 |
| 2007/0139735 A1 | 6/2007 | Shakespeare et al. | |

FOREIGN PATENT DOCUMENTS

| | | |
|---|---|---|
| JP | 2006-084333 A | 3/2006 |
| JP | 2006-129263 A | 5/2006 |
| JP | 2006-292510 A | 10/2006 |
| WO | 2007-078609 A1 | 7/2007 |

OTHER PUBLICATIONS

J. C. Zwinkels, et.al., "Instrumentation, standards, and procedures used at the National Research Council of Canada for high-accuracy fluorescence measurements" Analytica Chimica Acta, vol. 380, Issues 2-3, Feb. 2, 1999, pp. 193-209.

* cited by examiner

*Primary Examiner* — Kara E Geisel
(74) *Attorney, Agent, or Firm* — Canon USA Inc. IP Division

(57) ABSTRACT

A color processing apparatus according to the present invention is a color processing apparatus that calculates spectral reflectance including a fluorescent component in a sample under a target illuminant. The color processing apparatus includes first means for inputting, for each of a plurality of waveform types, spectral radiance including an excitation wavelength region and the amount of fluorescence in the sample corresponding to the spectral radiance; second means for determining, from spectral radiance of the target illuminant including the excitation wavelength region and the input spectral radiance and amount of fluorescence, the amount of fluorescence in the sample under the target illuminant; third means for inputting spectral reflectance excluding the fluorescent component in the sample; and fourth means for determining, by using the determined amount of fluorescence in the sample under the target illuminant and the input spectral reflectance excluding the fluorescent component in the sample, spectral reflectance including the fluorescent component in the sample under the target illuminant.

19 Claims, 20 Drawing Sheets

FIG. 6

| WAVELENGTH (nm) | SPECTRAL RADIANCE OF VIEWING ILLUMINANT (cd/m²) |
|---|---|
| 300 | xxx |
| 310 | xxx |
| 320 | xxx |
| ⋮ | ⋮ |
| 780 | xxx |

FIG. 7

| WAVELENGTH (nm) | SPECTRAL RADIANCE FOR WAVEFORM TYPE 1 (cd/m²) | SPECTRAL RADIANCE FOR WAVEFORM TYPE 2 (cd/m²) | SPECTRAL RADIANCE FOR WAVEFORM TYPE 3 (cd/m²) |
|---|---|---|---|
| 300 | xxx | xxx | xxx |
| 310 | xxx | xxx | xxx |
| 320 | xxx | xxx | xxx |
| ⋮ | ⋮ | ⋮ | ⋮ |
| 500 | xxx | xxx | xxx |

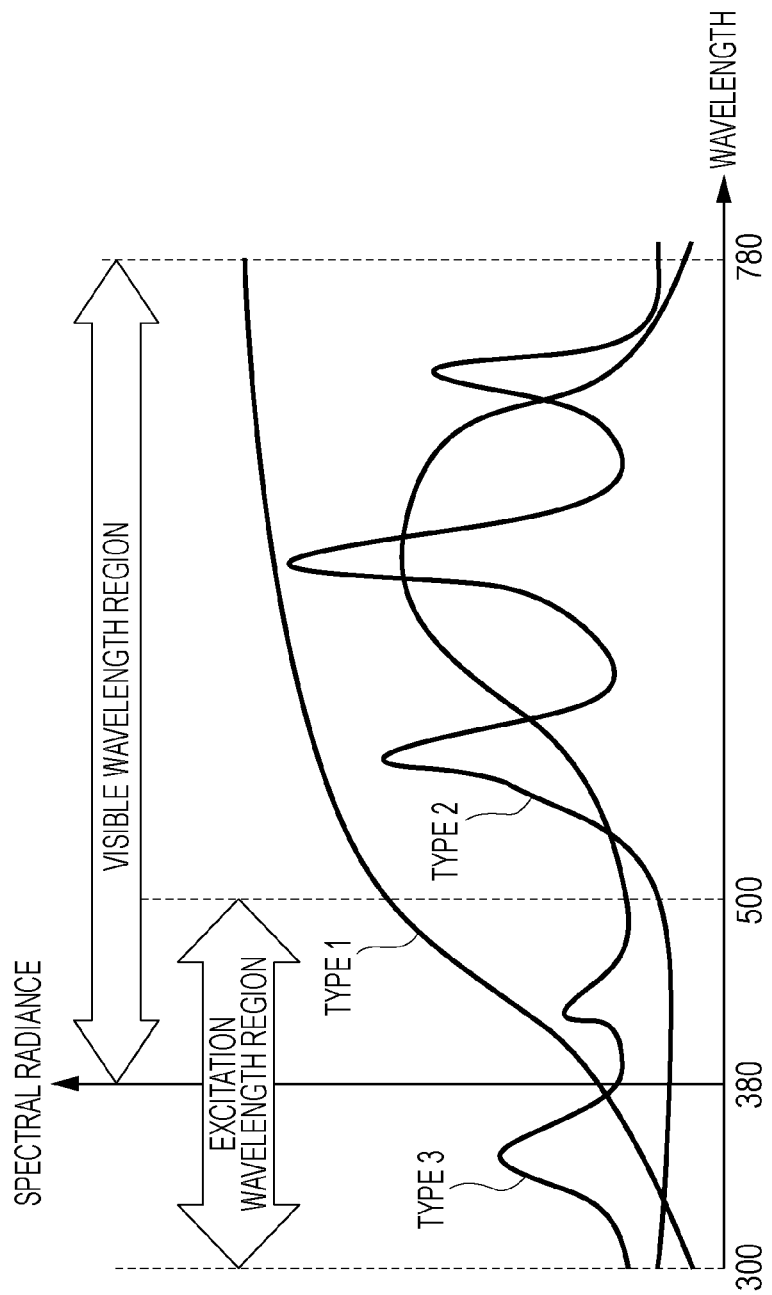

FIG. 9

| WAVELENGTH (nm) | SPECTRAL REFLECTANCE OF SAMPLE (EXCLUDING FLUORESCENCE) (%) | AMOUNT OF FLUORESCENCE FOR WAVEFORM TYPE 1 (%) | AMOUNT OF FLUORESCENCE FOR WAVEFORM TYPE 2 (%) | AMOUNT OF FLUORESCENCE FOR WAVEFORM TYPE 3 (%) |
|---|---|---|---|---|
| 380 | xxx | | | |
| 390 | xxx | | | |
| 400 | xxx | | | |
| ⋮ | ⋮ | xxx | xxx | xxx |
| | | xxx | xxx | xxx |
| | | xxx | xxx | xxx |
| | | xxx | xxx | xxx |
| | | xxx | xxx | xxx |
| | | xxx | xxx | xxx |
| ⋮ | ⋮ | | | |
| 770 | xxx | | | |
| 780 | xxx | | | |

R(λ) spans the spectral reflectance column; F(λ) spans the three fluorescence columns.

⟷ EMISSION WAVELENGTH REGION

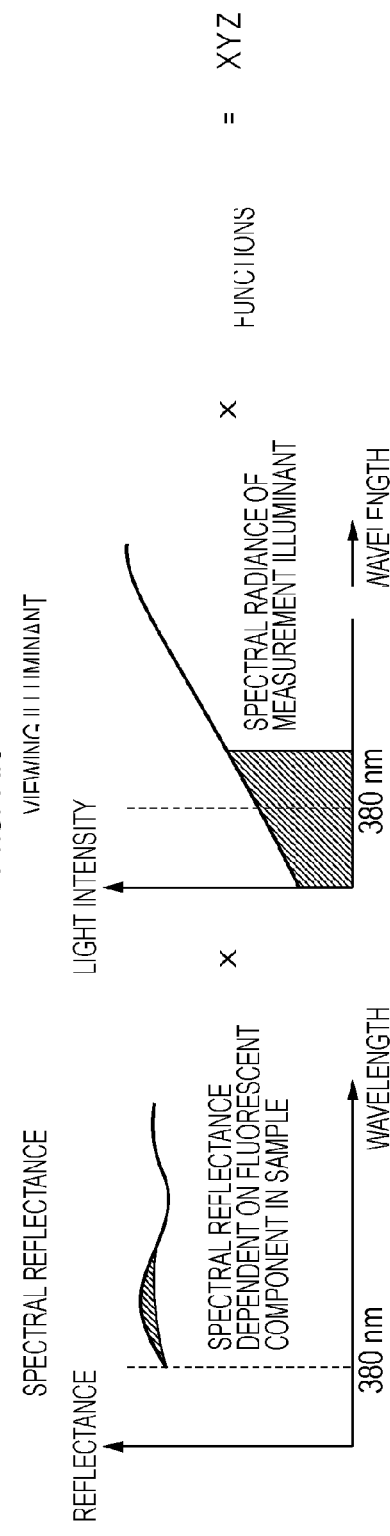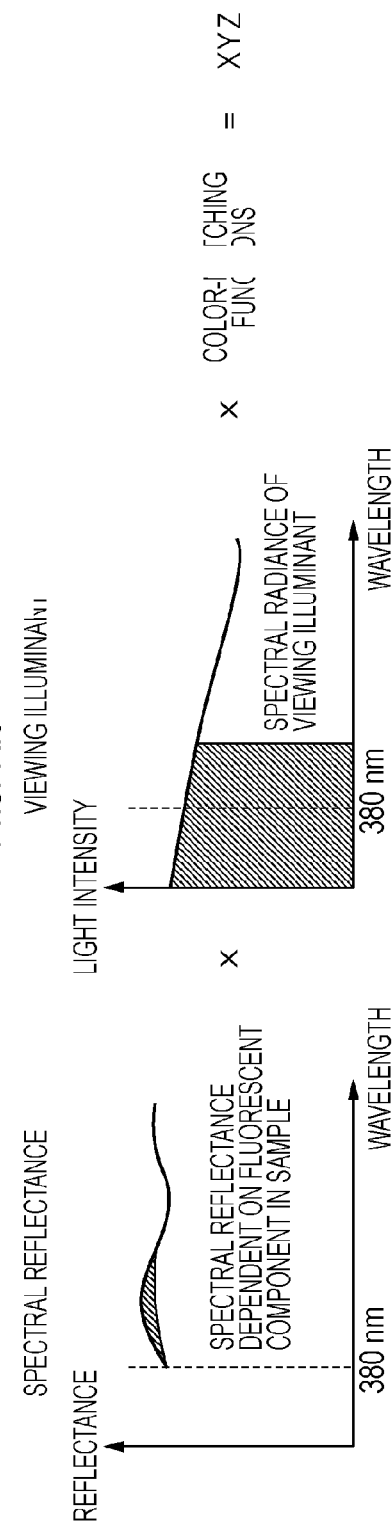

US 8,482,796 B2

COLOR PROCESSING APPARATUS AND COLOR PROCESSING METHOD

TECHNICAL FIELD

The present invention relates to color processing apparatuses and color processing methods for performing color processing in which a sample contains a fluorescent component.

BACKGROUND ART

In color matching where colors reproduced by an input device are matched with those reproduced by an output device, the colors reproduced by these devices are associated with each other on the basis of color reproduction characteristics of each device.

Generally, the color reproduction characteristics described above are calculated using a typical colorimeter illustrated in FIG. 18, in accordance with a procedure, such as that illustrated in FIG. 17. FIG. 17 illustrates an example of a procedure for calculating color reproduction characteristics of an image output device. First, a color chart is printed or output on a predetermined medium by the image output device. Then, spectral reflectance $R(\lambda)$ of the output color chart is measured by a colorimeter. In the colorimeter illustrated in FIG. 18, first, a sample (color chart) is irradiated with light from a colorimetric illuminant included in the colorimeter. The irradiation light is reflected by the sample. A photodetector receives spectral radiance of the reflected light through a spectroscope. Dividing the received spectral radiance of the reflected light by spectral radiance of the illuminant gives the spectral reflectance $R(\lambda)$ of the sample. Next, spectral radiance $S(\lambda)$ of an illuminant (viewing illuminant) under which an output image is viewed is measured. Then, CIE tristimulus values XYZ are calculated from the measured spectral reflectance $R(\lambda)$, the spectral radiance $S(\lambda)$ of the viewing illuminant, and color-matching functions $x(\lambda)$, $y(\lambda)$, and $z(\lambda)$ by using the following equations (1).

$$\begin{cases} X = k \int_{380}^{730} R(\lambda)S(\lambda)\bar{x}(\lambda)d\lambda \\ Y = k \int_{380}^{730} R(\lambda)S(\lambda)\bar{y}(\lambda)d\lambda \\ Z = k \int_{380}^{730} R(\lambda)S(\lambda)\bar{z}(\lambda)d\lambda \end{cases} \quad \text{equations (1)}$$

However, if a medium or ink contains a material (e.g., fluorescent whitener) that includes a fluorescent component, the spectral reflectance of the image output device measured by the foregoing method may be different from spectral reflectance under the viewing illuminant. Here, the fluorescent component is a component by which light in an excitation wavelength region, which is a predetermined wavelength region of irradiation light, is reflected in a different wavelength region (i.e., emission wavelength region).

Referring to FIG. 19, a description will be given of measurement in which spectral reflectance of a sample containing a fluorescent component is measured by the colorimeter illustrated in FIG. 18. When a colorimeter, such as that illustrated in FIG. 18, is used to measure a sample containing a fluorescent component, light in an excitation wavelength region reacts to the fluorescent component in the sample and is reflected in an emission wavelength region. Therefore, the reflected light received by the colorimeter is one that is affected by the amount of fluorescence which is dependent on the spectral radiance of the colorimetric illuminant in the excitation wavelength region. That is, spectral reflectance is also dependent on the colorimetric illuminant. Thus, as illustrated in FIG. 20A, when a colorimetric illuminant and a viewing illuminant are the same, since spectral radiance of the viewing illuminant in the excitation wavelength region corresponds to the amount of fluorescence, correct XYZ values can be calculated. On the other hand, as illustrated in FIG. 20B, when the colorimetric illuminant and the viewing illuminant are different, since the spectral radiance of the viewing illuminant in the excitation wavelength region does not correspond to the amount of fluorescence, correct XYZ values cannot be calculated. In other words, if an illuminant used to measure a sample containing a fluorescent component is different from an illuminant in an actual viewing environment, XYZ values, which are colorimetric values, do not correspond to the actual appearance of the color.

Japanese Patent Laid-Open No. 2006-84333 describes a method in which spectral reflectance of a sample under a viewing illuminant that is different from a colorimetric illuminant is estimated by taking a fluorescent component into account. Specifically, in this method, the spectral reflectance of the sample is measured under two different illuminants. Then, the spectral reflectance of the sample under the viewing illuminant is calculated on the basis of a ratio, in each of the illuminants, between the sum of spectral radiances in an excitation wavelength region and the sum of spectral radiances in an emission wavelength region.

However, the amount of fluorescence is not determined by the sum of spectral radiances in the excitation wavelength region. Therefore, even if the amount of fluorescence is calculated on the basis of the ratio between the sums as described above, it is not possible to determine, with high accuracy, the spectral reflectance under any viewing illuminant.

In view of the points described above, the present invention aims to determine, with high accuracy, colors of a sample containing a fluorescent component under any viewing illuminant.

SUMMARY OF INVENTION

A color processing apparatus according to the present invention is a color processing apparatus that calculates spectral reflectance including a fluorescent component in a sample under a target illuminant. The color processing apparatus includes first means for inputting, for each of a plurality of waveform types, spectral radiance including an excitation wavelength region and the amount of fluorescence in the sample corresponding to the spectral radiance; second means for determining, from spectral radiance of the target illuminant including the excitation wavelength region and the input spectral radiance and amount of fluorescence, the amount of fluorescence in the sample under the target illuminant; third means for inputting spectral reflectance excluding the fluorescent component in the sample; and fourth means for determining, by using the determined amount of fluorescence in the sample under the target illuminant and the input spectral reflectance excluding the fluorescent component in the sample, spectral reflectance including the fluorescent component in the sample under the target illuminant.

A color processing method according to the present invention is a color processing method for calculating spectral reflectance including a fluorescent component in a sample under a target illuminant. The color processing method includes a first step of inputting, for each of a plurality of waveform types, spectral radiance including an excitation wavelength region and the amount of fluorescence in the sample corresponding to the spectral radiance; a second step of determining, from spectral radiance of the target illuminant including the excitation wavelength region and the input spectral radiance and amount of fluorescence, the amount of fluorescence in the sample under the target illuminant; a third step of inputting spectral reflectance excluding the fluorescent component in the sample; and a fourth step of determining, by using the determined amount of fluorescence in the sample under the target illuminant and the input spectral reflectance excluding the fluorescent component in the sample, spectral reflectance including the fluorescent component in the sample under the target illuminant.

Further features of the present invention will become apparent from the following description of exemplary embodiments with reference to the attached drawings.

BRIEF DESCRIPTION OF DRAWINGS

FIG. 6 shows an example of spectral radiance of a viewing illuminant.

FIG. 7 shows an example of spectral radiance for each waveform type.

FIG. 8 illustrates an example of waveform types.

FIG. 9 shows an example of spectral reflectance excluding fluorescence in a sample, and the amount of fluorescence corresponding to each waveform type.

FIG. 20A and FIG. 20B illustrate a relationship between calculation of XYZ values and illuminants.

DESCRIPTION OF EMBODIMENTS

First Embodiment

Figure 1A:
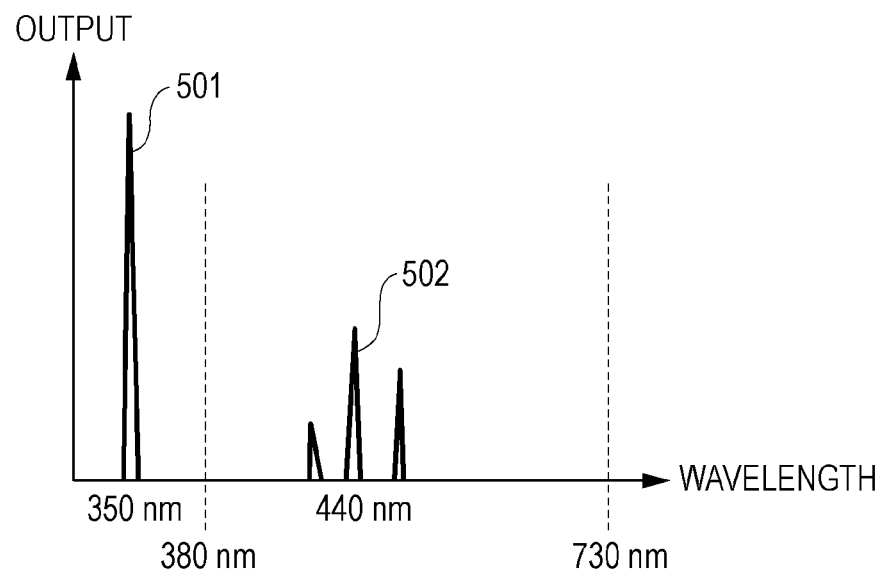
FIG. 1A and FIG. 1B are conceptual diagrams illustrating principles of fluorescence.
Figure 1B:
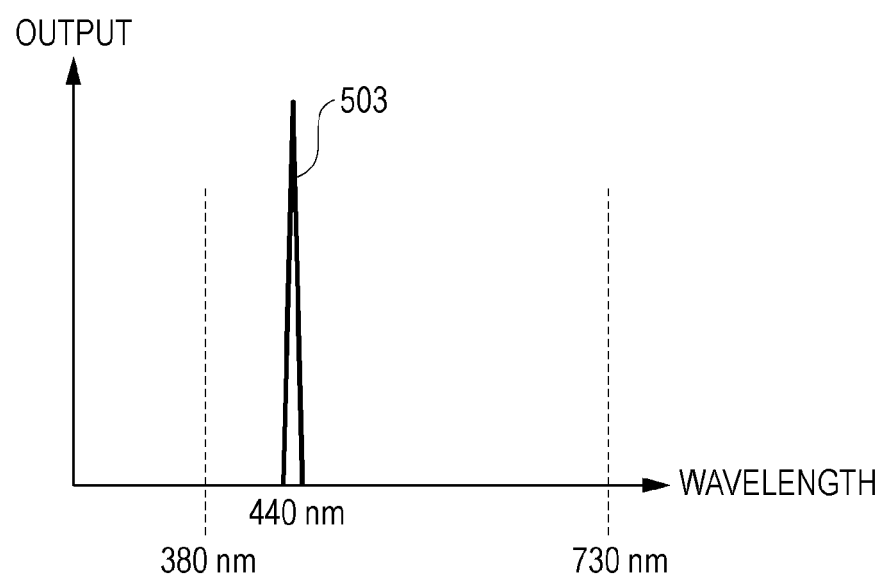

First, a fluorescent component will be described with reference to FIG. 1A and FIG. 1B. Here, the fluorescent component is a component by which light in an excitation wavelength region, which is a predetermined wavelength region of irradiation light, is emitted in a different wavelength region (i.e., emission wavelength region). FIG. 1A illustrates the intensity of light reflected from a sample when the sample is irradiated with monochromatic light with a wavelength of 350 nm. In the drawing, reference numeral 501 denotes reflected light with a wavelength of 350 nm corresponding to the monochromatic light with a wavelength of 350 nm, and reference numeral 502 denotes fluorescence emitted at a wavelength of 440 nm by a fluorescent component excited by the monochromatic light with a wavelength of 350 nm. FIG. 1B illustrates the intensity of light reflected from the sample when the sample is irradiated with monochromatic light with a wavelength of 440 nm. In the drawing, reference numeral 503 denotes reflected light with a wavelength of 440 nm corresponding to the monochromatic light with a wavelength of 440 nm.

When a sample contains a fluorescent component, if the sample is irradiated with light of an excitation wavelength as shown in FIG. 1A, emission of light is observed at wavelengths different from that of the irradiation light, along with the reflected light of the wavelength of the irradiation light. On the other hand, if the sample is irradiated with light of a wavelength which is not an excitation wavelength, the reflected light of the wavelength of the irradiation light is observed. Therefore, under an illuminant having wavelength components of both 350 nm and 440 nm, light with a wavelength of 440 nm observed from the sample is the sum of the emitted light 502 and the reflected light 503. Since a typical illuminant has many wavelength components, the sum of the reflected light and the emitted light at a wavelength of 440 nm for all the wavelengths is light with a wavelength of 440 nm observed from the sample under the illuminant.

As described above, to obtain accurate colorimetric values of a sample containing a fluorescent component in any viewing environment, it is necessary to take into account fluorescence that is dependent on light in the excitation wavelength region of irradiation light. Hereinafter, a description will be given of a color processing apparatus that estimates spectral reflectance of a sample in accordance with the waveform of light of a viewing illuminant (target illuminant) in an excitation wavelength region, and obtains accurate colorimetric values of the sample.

In the present embodiment, a description will be given of a process in which XYZ values of the sample under the viewing illuminant are calculated on the basis of the following data held in advance: spectral radiance of the viewing illuminant, spectral radiance for each waveform type in excitation wavelengths, and spectral reflectance of the sample and the amount of fluorescence. Each of the data will be described in detail later on.

Figure 2:
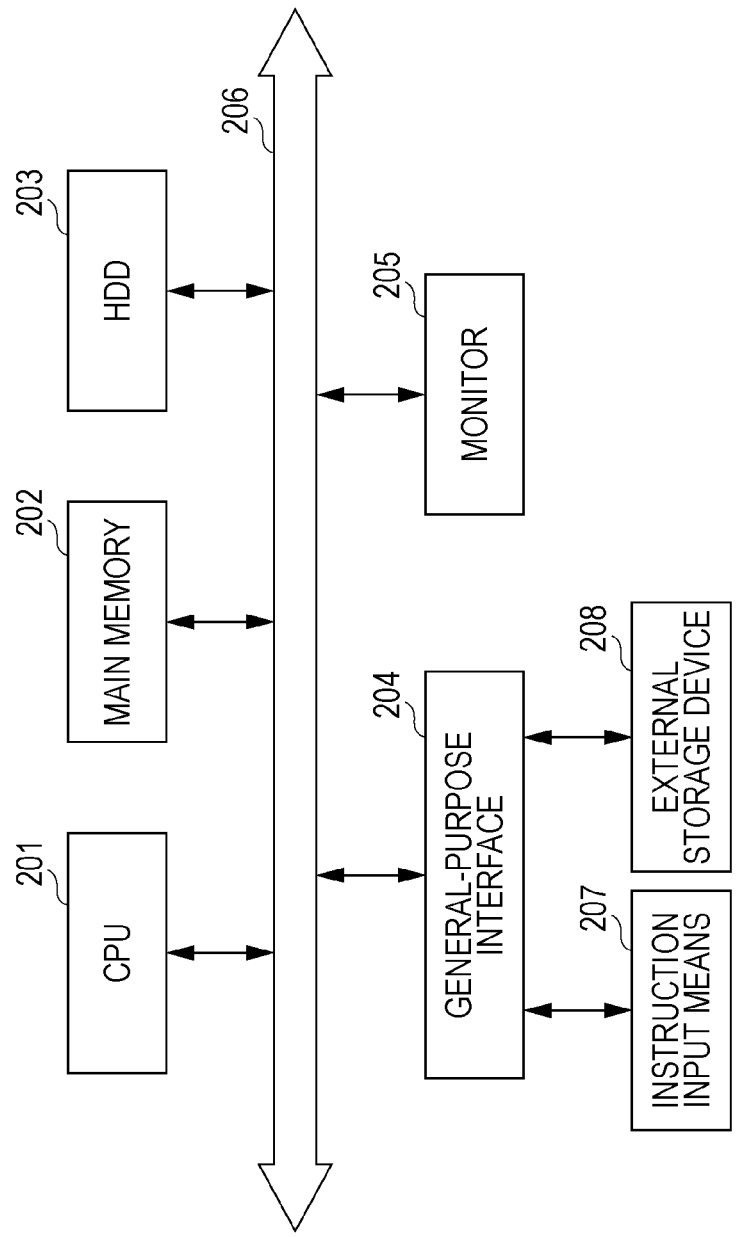
FIG. 2 illustrates a configuration of a color processing apparatus.

FIG. 2 illustrates a configuration of a color processing apparatus according to the present embodiment. The color processing apparatus includes a CPU 201, a main memory 202, an HDD 203, a general-purpose interface 204, a monitor 205, a main bus 206, an instruction input unit 207 including a keyboard and a mouse, and an external storage device 208. The general-purpose interface 204 allows the instruction input unit 207 and the external storage device 208 to connect to the main bus 206.

Hereinafter, a description will be given of various processes realized when various software programs (computer programs), including a color processing application, stored in the HDD 203 are operated by the CPU 201.

First, in response to a user instruction input from the instruction input unit 207, the CPU 201 starts a color processing application stored in the HDD 203 or the external storage device 208. The CPU 201 opens the color processing application in the main memory 202 and displays a user interface on the monitor 205. Next, in accordance with a command from the CPU 201, various data stored in the HDD 203 or the external storage device 208 is transferred through the main bus 206 to the main memory 202. Then, the various data transferred to the main memory 202 is subjected to predetermined calculations in accordance with a command from the CPU 201. Results of the calculations are displayed on the monitor 205 or stored in the HDD 203 or the external storage device 208 through the main bus 206.

A description will be given of a process in which, in the configuration described above, the color processing application calculates colorimetric values under a viewing illuminant in accordance with a command from the CPU 201.

Figure 3:
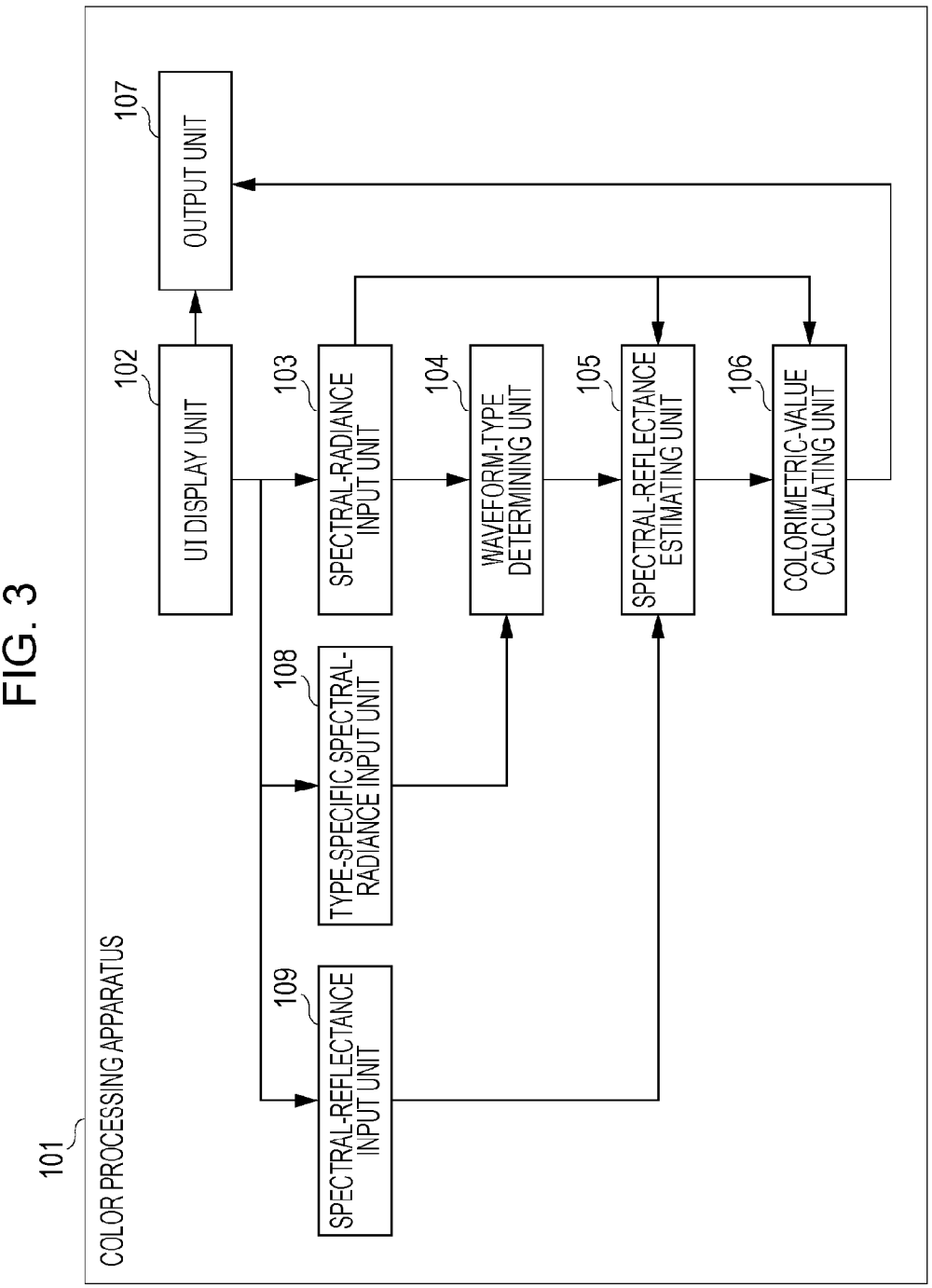
FIG. 3 illustrates a functional configuration of the color processing apparatus.

FIG. 3 illustrates a functional configuration of a color processing apparatus according to the present embodiment. As described above, in the present embodiment, the configuration illustrated in FIG. 3 is realized as color processing application software.

Referring to FIG. 3, a color processing apparatus 101 includes a display unit 102, a spectral-radiance input unit 103, a waveform-type determining unit 104, a spectral-reflectance estimating unit 105, a colorimetric-value calculating unit 106, an output unit 107, a type-specific spectral-radiance input unit 108, and a spectral-reflectance input unit 109. The display unit 102 displays a user interface etc. on the monitor 205. The spectral-radiance input unit 103 inputs spectral radiance of a viewing illuminant. The waveform-type determining unit 104 determines a waveform type of the viewing illuminant in an excitation wavelength region. The spectral-reflectance estimating unit 105 estimates spectral reflectance of a sample under the viewing illuminant. The colorimetric-value calculating unit 106 calculates CIE tristimulus values XYZ from the spectral reflectance of the sample and the spectral radiance of the viewing illuminant. The output unit 107 outputs, as a file, the colorimetric values calculated by the colorimetric-value calculating unit 106 to the HDD 203 or the external storage device 208. The type-specific spectral-radiance input unit 108 inputs, for each of a plurality of waveform types identified in advance, spectral radiance in excitation wavelengths. The spectral-reflectance input unit 109 inputs spectral reflectance from which the effect of a fluorescent component in the sample is eliminated (i.e., spectral reflectance excluding fluorescence). At the same time, the spectral-reflectance input unit 109, which serves as an obtaining means for obtaining the amount of fluorescence, inputs the amount of fluorescence for each waveform type.

<Operation in Color Processing Apparatus 101>

Figure 4:
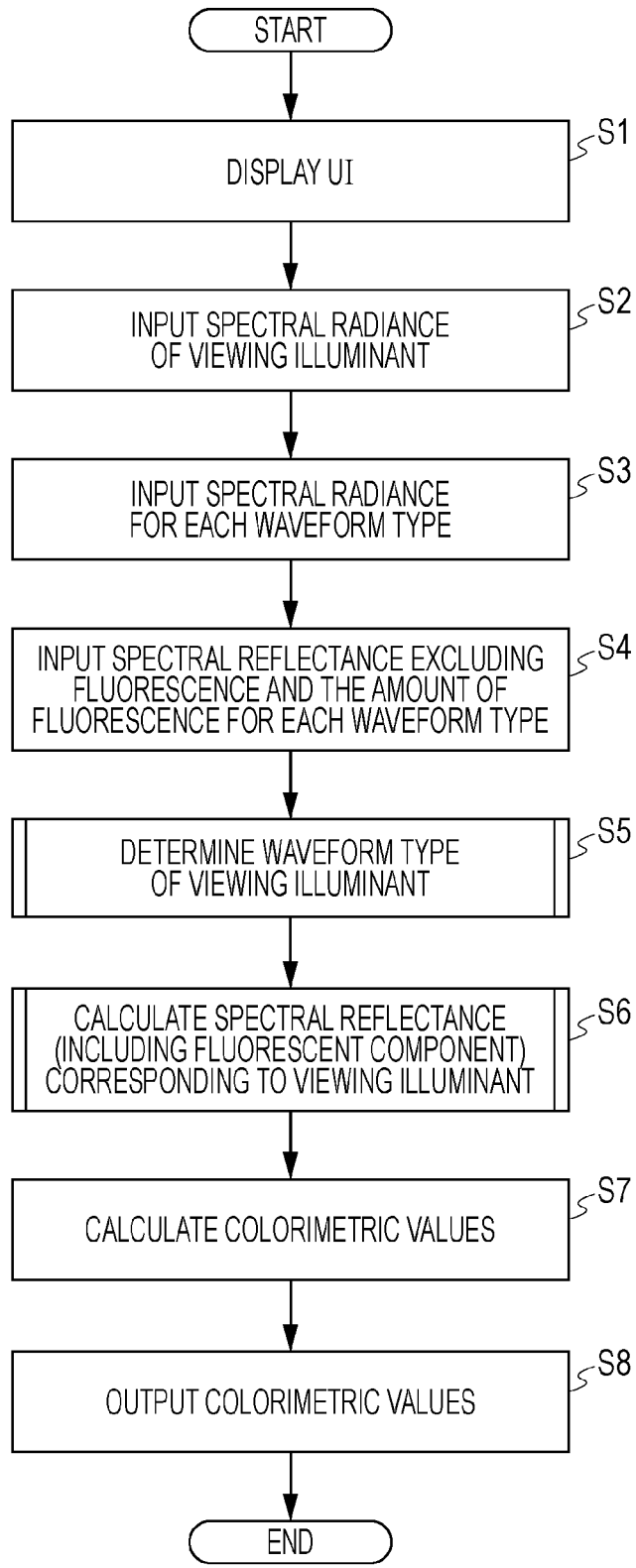
FIG. 4 is a flowchart of a process in the color processing apparatus.

FIG. 4 is a flowchart of a process performed in the color processing apparatus 101.

Figure 5:
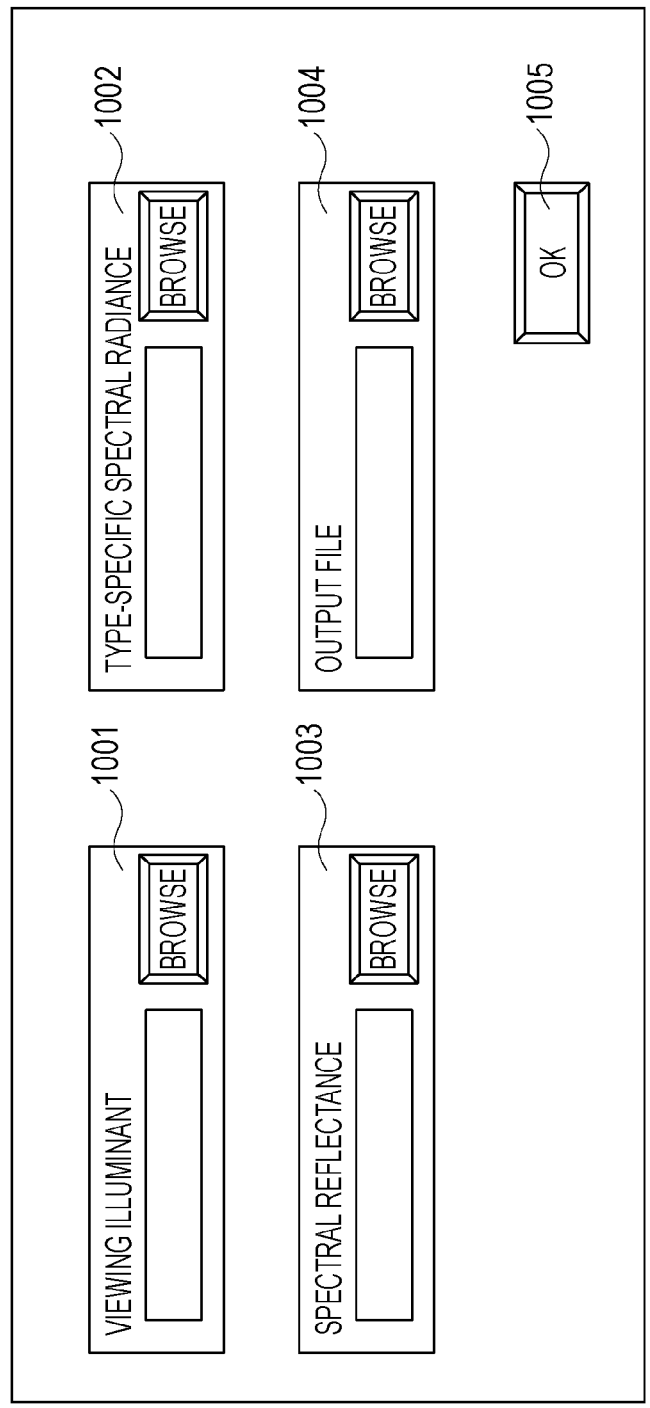
FIG. 5 illustrates a user interface displayed by a UI display unit.

In step S1, the UI display unit 102 displays a user interface on the monitor 205 to prompt the user to input information necessary for color processing. An example of such a user interface displayed is illustrated in FIG. 5. An input section 1001 is for specifying spectral radiance of a viewing illuminant. An input section 1002 is for specifying spectral radiance for each of a plurality of waveform types identified in advance. An input section 1003 is for specifying spectral reflectance excluding fluorescence in a sample, and the amount of fluorescence for each waveform type. An input section 1004 is for specifying a file name for saving colorimetric values of a sample calculated in the color processing apparatus 101. A button 1005 is an OK button used to issue an instruction to execute a process in the color processing apparatus 101. In response to the execution instruction issued with this button, the process proceeds to step S2. The user interface illustrated in FIG. 5 is merely an example, and any user interface may be used, as long as it allows the user to specify spectral radiance of a viewing illuminant, spectral radiance for each waveform type, spectral reflectance excluding fluorescence in a sample, and the amount of fluorescence for each waveform type.

In step S2, on the basis of a file name specified in the input section 1001 of the user interface displayed in step S1, the spectral-radiance input unit 103 inputs spectral radiance of a viewing illuminant from the HDD 203 or the external storage device 208. Generally, a wavelength range of light visible to the human eye (i.e., visible wavelength region) is from 380 nm to 780 nm. Since a fluorescent component in a sample is taken into account in the present embodiment, spectral radiance including an excitation wavelength region is input. Note that an excitation wavelength region of a fluorescent component in a sample is determined, for example, by a material, such as a fluorescent whitener, which is applied to a print medium. In the present embodiment, the following process will be described with reference to an example in which the excitation wavelength region is from 300 nm to 500 nm. FIG. 6 shows a data structure of spectral radiance of an illuminant, specified by the user. As shown in FIG. 6, spectral radiance values measured for wavelengths from 300 nm to 780 nm in 10 nm steps are specified by the user.

In step S3, on the basis of a file name specified in the input section 1002 of the user interface displayed in step S1, the type-specific spectral-radiance input unit 108 inputs spectral radiance for each waveform type from the HDD 203 or the external storage device 208. FIG. 7 shows an example of type-specific spectral radiance specified by the user. As shown in FIG. 7, spectral radiance values of a plurality of illuminants classified, in advance, by the shape of their waveform in the excitation wavelength region are saved in a file. The present embodiment describes an example in which waveforms in the excitation wavelength region are classified into three distinctive types by shape. FIG. 8 illustrates an example of waveform types of illuminants classified. As illustrated in FIG. 8, in the excitation wavelength region, a plurality of illuminants of different waveform types, which are patterns of waveform shapes, are classified in advance into typical waveform types, such as type 1 to type 3. For example, such classification is done by measuring the spectral radiance of various illuminants, such as a fluorescent lamp, an LED, and an electric lamp, in the excitation wavelength region in advance, and grouping illuminants of similar waveforms together.

Figure 10:
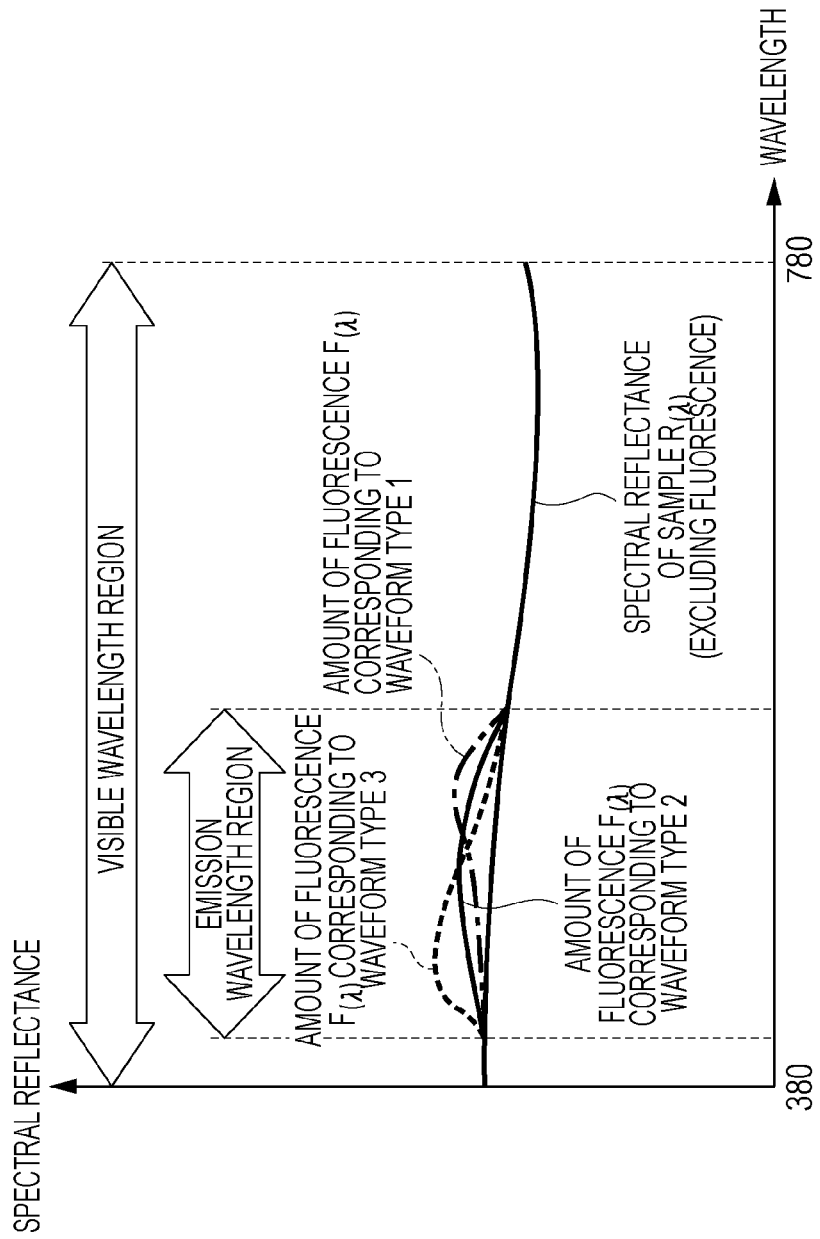
FIG. 10 shows a relationship between spectral reflectance excluding fluorescence and the amount of fluorescence for each waveform type.

In step S4, on the basis of a file name specified in the input section 1003 of the user interface displayed in step S1, the spectral-reflectance input unit 109 obtains spectral reflectance of the sample from the HDD 203 or the external storage device 208. FIG. 9 shows an example of spectral reflectance of the sample, specified by the user. As shown in FIG. 9, in the file specified by the user, values of spectral reflectance $R(\lambda)$ excluding fluorescence in the sample and values of the amount of fluorescence $F(\lambda)$ for each waveform type are saved. The spectral reflectance $R(\lambda)$ excluding fluorescence and the amount of fluorescence $F(\lambda)$ for each waveform type have a relationship illustrated in FIG. 10. The amount of fluorescence $F(\lambda)$ varies depending on the waveform type of the illuminant.

Figure 11:
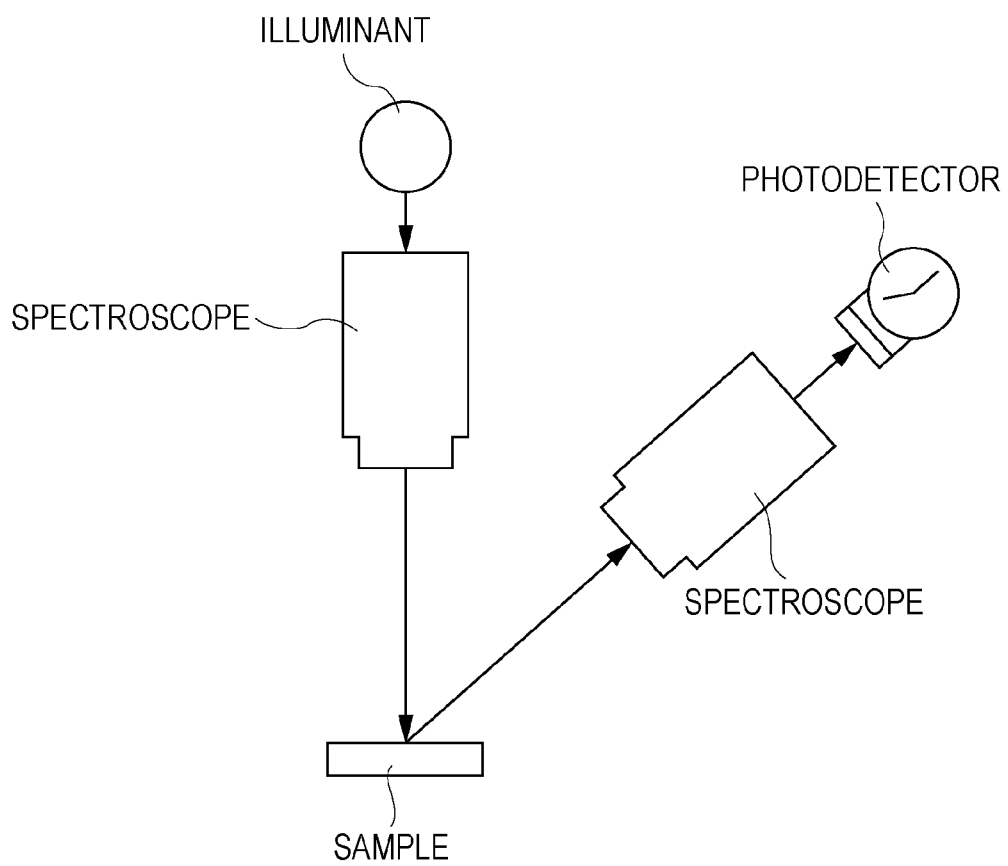
FIG. 11 illustrates an example of a method in which, when monochromatic light is incident on a sample, the reflected light of each wavelength is measured.

The spectral reflectance $R(\lambda)$ excluding fluorescence can be measured, for example, by using a measurement method illustrated in FIG. 11. First, a sample is irradiated with monochromatic light emitted from an illuminant and passed through a spectroscope. Then, of beams of light reflected from the sample, only monochromatic light same as the irradiation light is passed through another spectroscope and received by the photodetector. With this method of measurement, it is possible to separate fluorescence from reflected light and perform measurement excluding the effect of fluorescence. This measurement can be performed for wavelengths in the visible wavelength region and the measurement results can be saved in a file.

Figure 18:
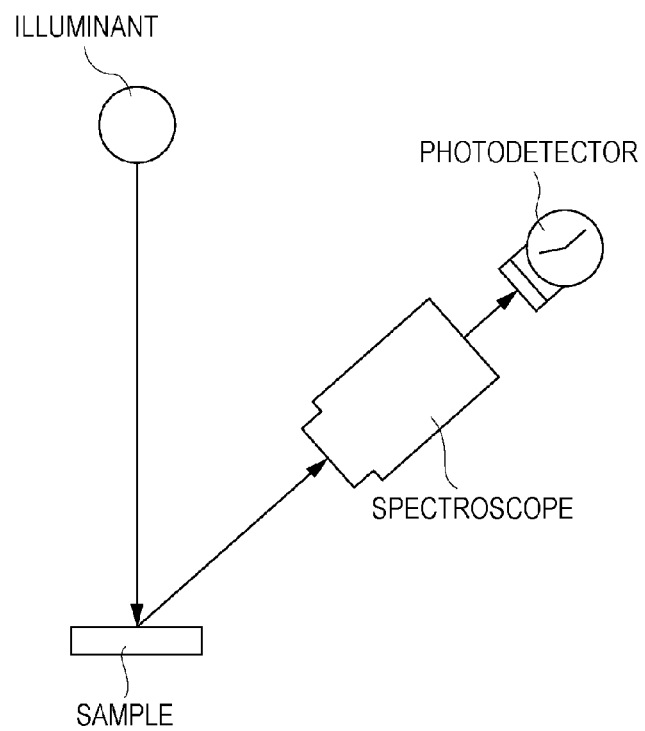
FIG. 18 illustrates an example of a typical colorimeter.
Figure 19:
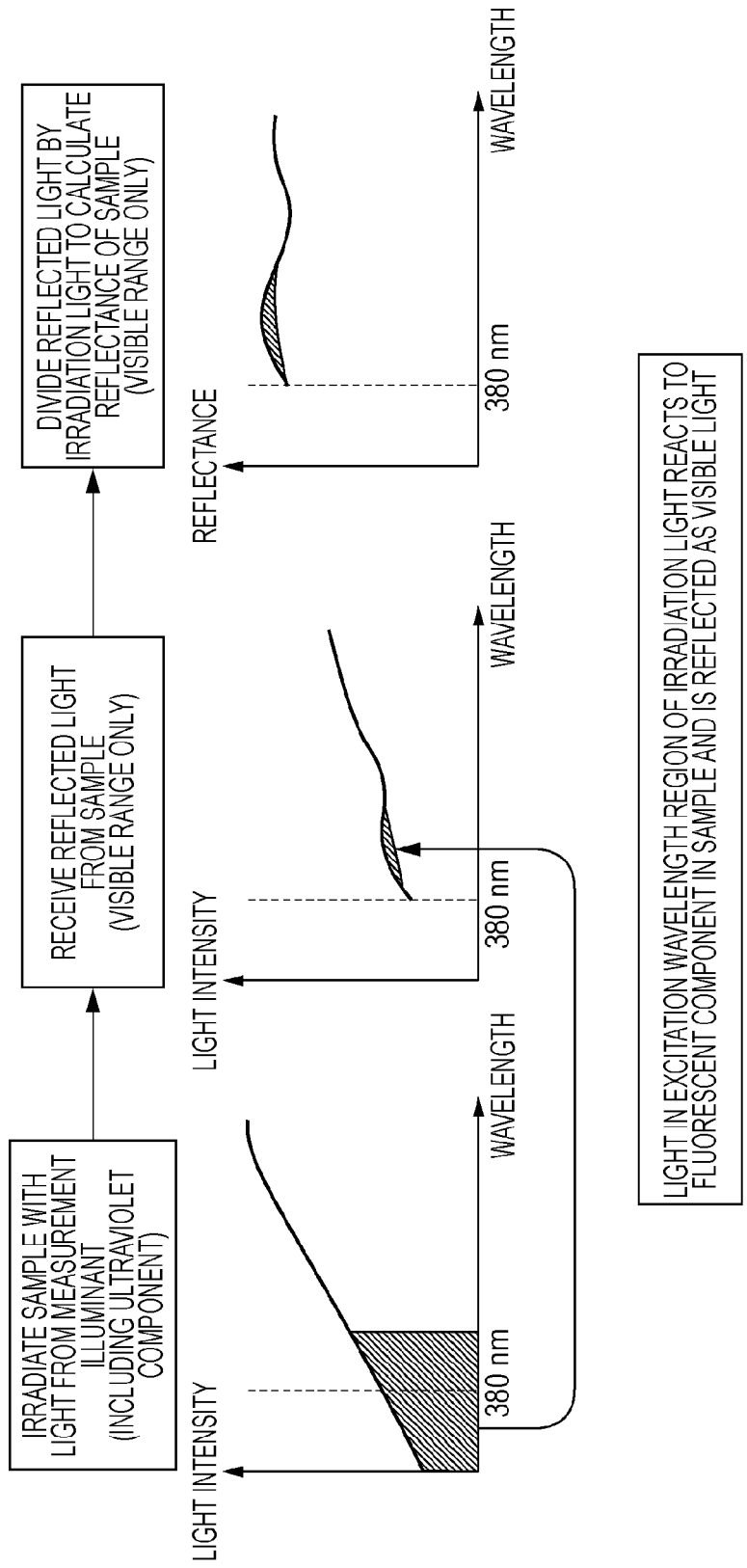
FIG. 19 illustrates a flow of spectral reflectance measurement performed using a typical colorimeter.

The amount of fluorescence F(λ) can be determined by calculating a difference between spectral reflectance including fluorescence obtained by typical measurement, such as that illustrated in FIG. 18, and spectral reflectance excluding fluorescence. For each waveform type, spectral reflectance including fluorescence is measured, spectral reflectance excluding fluorescence is subtracted from the spectral reflectance including fluorescence, and the result of the subtraction is saved in a file. Since the wavelength region in which fluorescence is emitted (i.e., emission wavelength region) is determined by the material of the sample, the amount of fluorescence F(λ) for only the emission wavelength region can be held, as illustrated in FIG. 9.

In step S5, the waveform-type determining unit 104 determines the waveform type of the viewing illuminant whose spectral radiance is input in step S2. The process performed by the waveform-type determining unit 104 will be specifically described later on.

In step S6, on the basis of the waveform type determined in step S5 and the spectral radiance of the viewing illuminant in the excitation wavelength region, the spectral-reflectance estimating unit 105 estimates spectral reflectance corresponding to the viewing illuminant. The process performed by the spectral-reflectance estimating unit 105 will be specifically described later on.

In step S7, from the spectral reflectance estimated in step S6 and the spectral radiance of the viewing illuminant, the colorimetric-value calculating unit 106 calculates colorimetric values. In the present embodiment, colorimetric values are CIE tristimulus values, which are calculated using equations (1) described above.

In step S8, the output unit 107 stores the colorimetric values calculated in step S7 in the HDD 203 or the external storage device 208 with an output file name specified in the input section 1004. Then, the process ends.

<Operation of Waveform-Type Determining Unit 104 (Step S5)>

Figure 12:
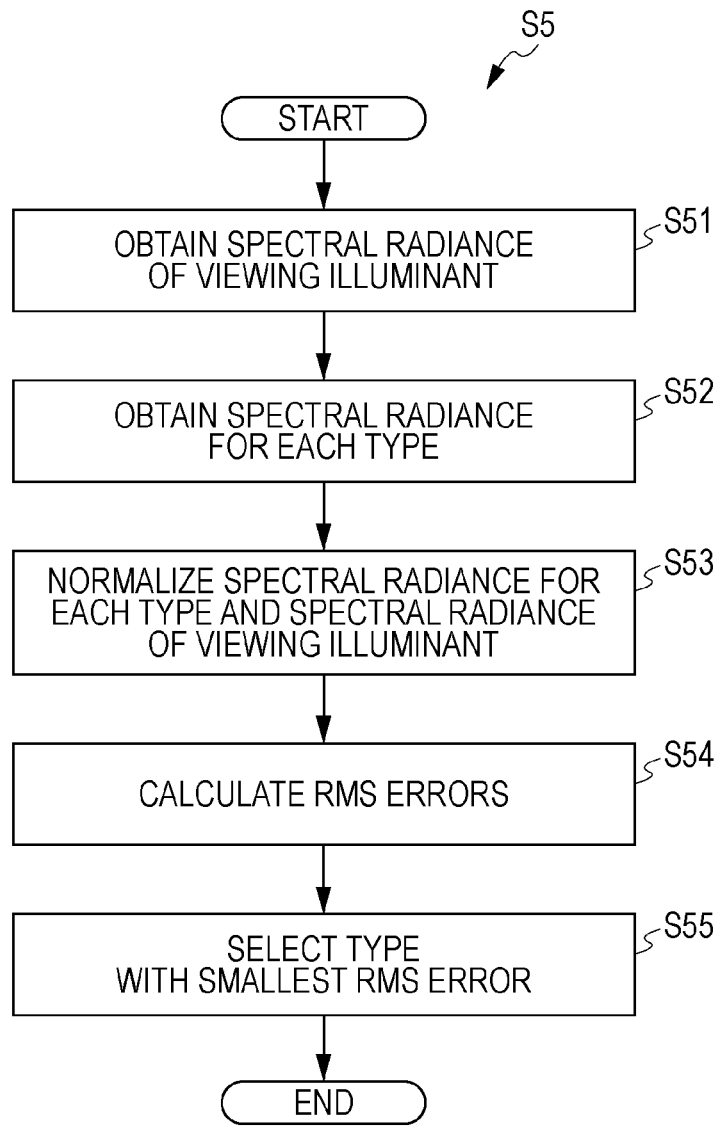
FIG. 12 is a flowchart illustrating a process of determining a waveform type.

FIG. 12 is a flowchart illustrating a process of determining a waveform type in step S5 of FIG. 4.

In step S51, the spectral radiance of the viewing illuminant (input in step S2 of FIG. 4) is obtained.

In step S52, the spectral radiance for each waveform type (input in step S3 of FIG. 4) is obtained.

In step S53, the spectral radiance for each waveform type (in the excitation wavelength region) obtained in step S52 and the spectral radiance of the viewing illuminant (in the excitation wavelength region) obtained in step S51 are normalized. The normalization is done by dividing the spectral radiance of each illuminant by an integral of spectral radiance of the illuminant in the excitation wavelength region. Specifically, the following equation (2) is applied to all radiances in the excitation wavelength region. In the equation, S(λ) is spectral radiance of each illuminant and S'(λ) is normalized spectral radiance of each illuminant.

$$S'(\lambda) = \frac{S(\lambda)}{\int_{300}^{500} S(\lambda) d\lambda} \quad \text{equation (2)}$$

In step S54, the normalized spectral radiance of the viewing illuminant and the normalized spectral radiance for each waveform type, which are obtained in step S53, are compared to each other to calculate an RMS error therebetween using the following equation (3). In the equation, S'$_v$(λ) is normalized spectral radiance of the viewing illuminant, S'$_{type\_i}$(λ) is normalized spectral radiance of a type i illuminant, and E$_{type\_i}$ is an RMS error between them.

$$E_{type\_i} = \int_{300}^{500} \sqrt{(S'_v(\lambda) - S'_{type\_i}(\lambda))^2} d\lambda \quad \text{equation (3)}$$

This RMS error calculation is performed for each waveform type. Since there are three waveform types in the present embodiment, this RMS error calculation is performed three times.

In step S55, the waveform type of the viewing illuminant in the excitation wavelength region is determined. Specifically, a waveform type for which the RMS error calculated in step S54 is the smallest is selected as the waveform type of the viewing illuminant. The process thus ends. In the present embodiment, the following process will be described on the assumption that the waveform type of the viewing illuminant is type 3.

<Operation of Spectral-Reflectance Estimating Unit 105 (Step S6)>

Figure 13:
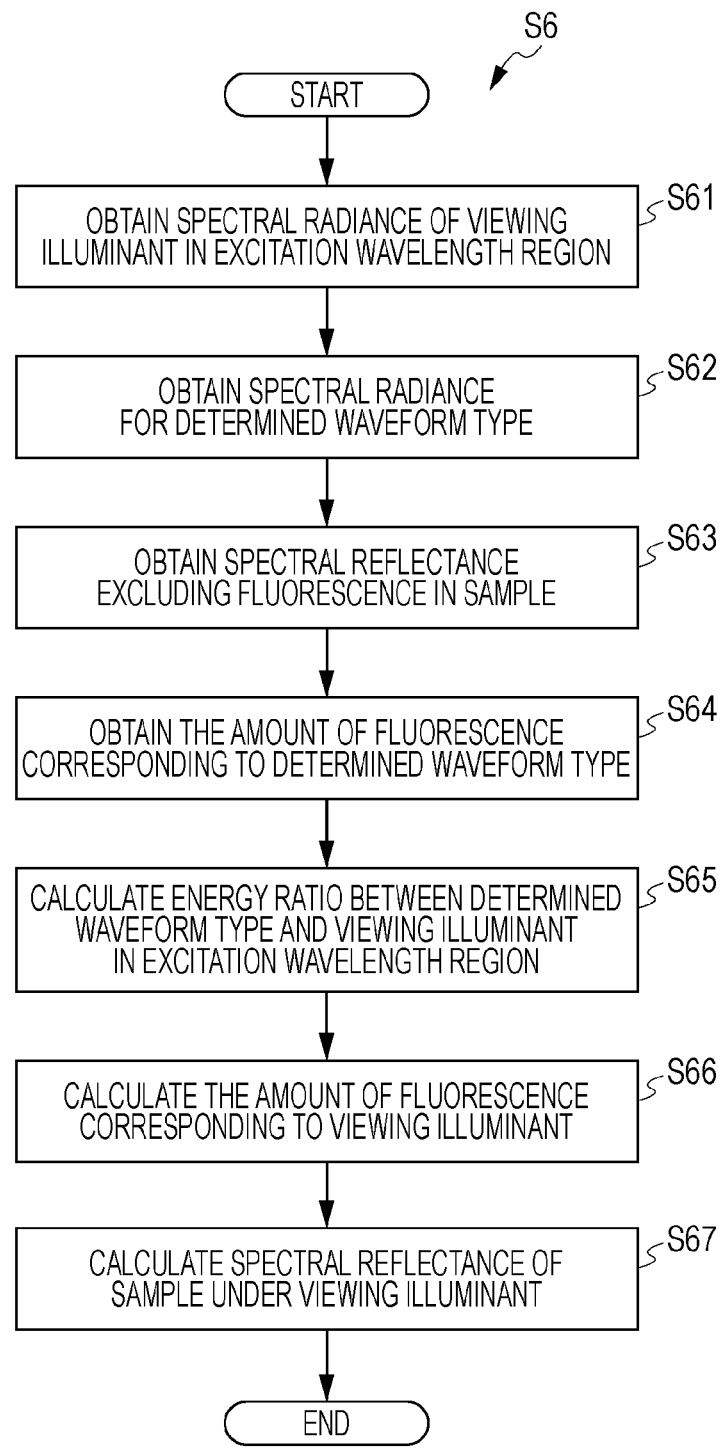
FIG. 13 is a flowchart illustrating a process of estimating spectral reflectance.

FIG. 13 is a flowchart illustrating a process of estimating spectral reflectance in step S6 of FIG. 4.

In step S61, the spectral radiance S$_v$(λ) of the viewing illuminant (input in step S2 of FIG. 4) is obtained.

In step S62, from the spectral radiance for each waveform type (input in step S3 of FIG. 4), spectral radiance for the waveform type of the viewing illuminant (determined in step S5 of FIG. 4) is obtained. Since the waveform type of the viewing illuminant is type 3 in the present embodiment, spectral radiance S$_{type\_3}$(λ) for type 3 is obtained.

In step S63, the spectral reflectance R(λ) excluding fluorescence in the sample (input in step S4 of FIG. 4) is obtained.

In step S64, of the amounts of fluorescence F(λ) for the respective waveform types (input in step S4 of FIG. 4), the amount of fluorescence corresponding to the waveform type for which the spectral radiance has been obtained in step S62 is obtained. Since the waveform type of the viewing illuminant is type 3 in the present embodiment, the amount of fluorescence F$_{type\_3}$(λ) corresponding to type 3 is obtained.

In step S65, from the spectral radiance S$_v$(λ) of the viewing illuminant (obtained in step S61) and the spectral radiance S$_{type\_3}$(λ) for type 3 (obtained in step S62), an energy ratio "ratio" is calculated using equation (4). The calculation of the energy ratio "ratio" is performed for the excitation wavelength region only.

$$\text{ratio} = \frac{\int_{300}^{500} S_v(\lambda) d\lambda}{\int_{300}^{500} S_{type\_3}(\lambda) d\lambda} \quad \text{equation (4)}$$

In step S66, on the basis of the amount of fluorescence F$_{type\_3}$ for type 3 (obtained in step S64) and the energy ratio "ratio" (calculated in step S65), the amount of fluorescence F$_v$(λ) corresponding to the viewing illuminant is calculated. Specifically, the calculation is done by applying the following equation (5) to all wavelengths in the emission wavelength region.

$$F_v(\lambda) = F_{type\_3}(\lambda) \times \text{ratio} \quad \text{equation (5)}$$

In step S67, the amount of fluorescence F$_v$(λ) corresponding to the viewing illuminant (calculated in step S66) is added to the spectral reflectance R(λ) excluding fluorescence in the sample (obtained in step S63). Specifically, spectral reflectance R$_v$(λ) under the viewing illuminant is calculated using the following equation (6). The process thus ends.

$$R_v(\lambda)=R(\lambda)+F_v(\lambda) \quad \text{equation (6)}$$

As described above, in the present embodiment, on the basis of the waveform type and spectral radiance of the viewing illuminant in the excitation wavelength region, it is possible to estimate spectral reflectance that takes into account the effect of a fluorescent component under any viewing illuminant. Therefore, it is possible to calculate colorimetric values that take into account the appearance of the sample containing a fluorescent component under any viewing illuminant.

Second Embodiment

The first embodiment has been described using an example in which, on the basis of data stored in the HDD 203 or the external storage device 208, an application calculates XYZ values of a sample under a viewing illuminant. In a second embodiment, such XYZ values are calculated not by processing data stored in advance, but by controlling a colorimeter in accordance with an instruction of a colorimetric application connected to the colorimeter. Here, differences from the first embodiment will be described, and the description of the same points as those in the first embodiment will be omitted.

Figure 14:
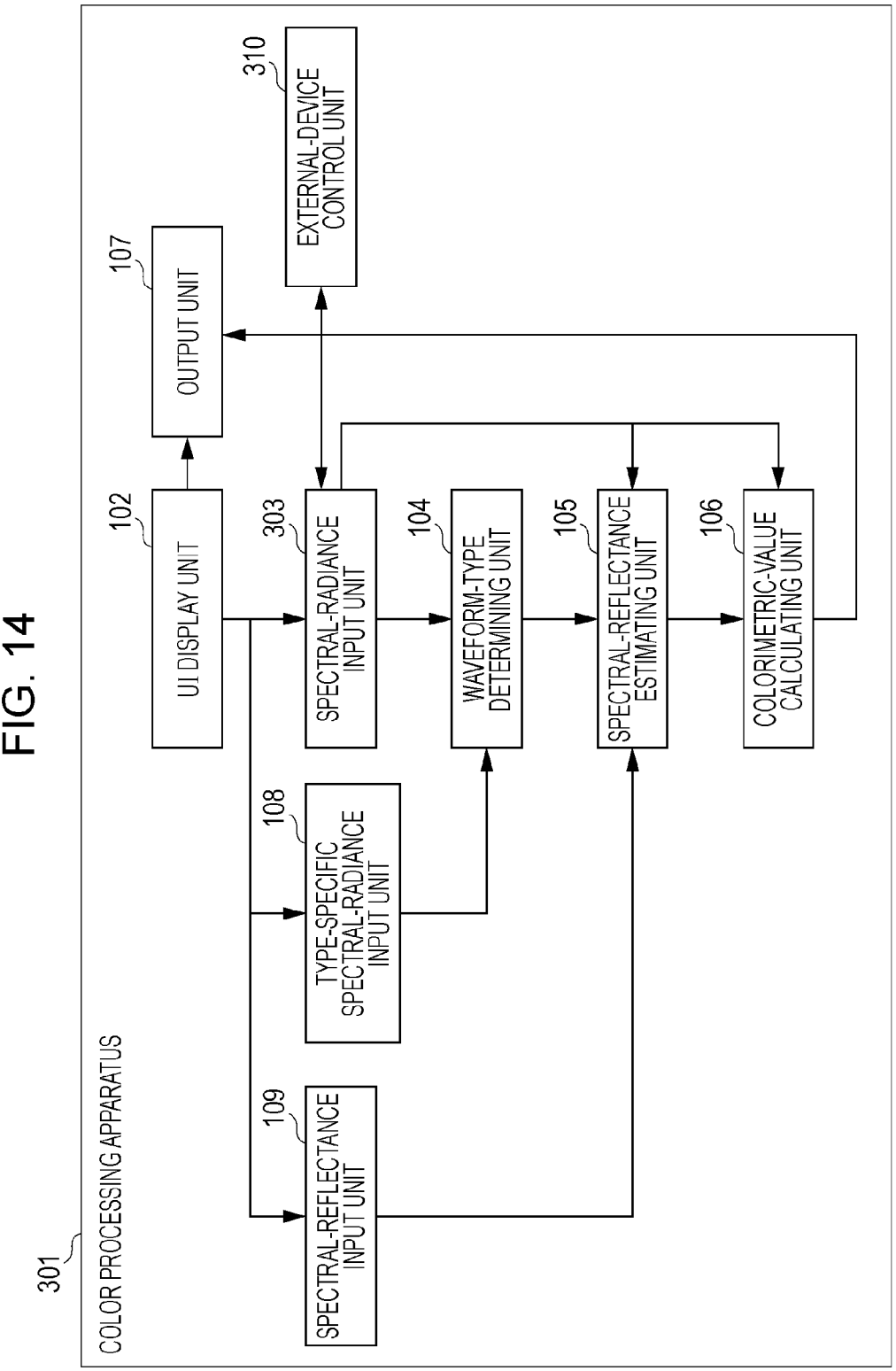
FIG. 14 illustrates a configuration of a color processing apparatus according to a second embodiment.

FIG. 14 illustrates a configuration of a color processing apparatus 301 according to the second embodiment. In FIG. 14, differences from the first embodiment are that there are a spectral-radiance input unit 303 and an external-device control unit 310 that controls a colorimeter. The external-device control unit 310 of the present embodiment can be realized, for example, as a device driver on a general-purpose OS.

Hereinafter, an operation of inputting spectral radiance of a viewing illuminant in the first embodiment (in step S2 of FIG. 4) will be described in detail.

Figure 15:
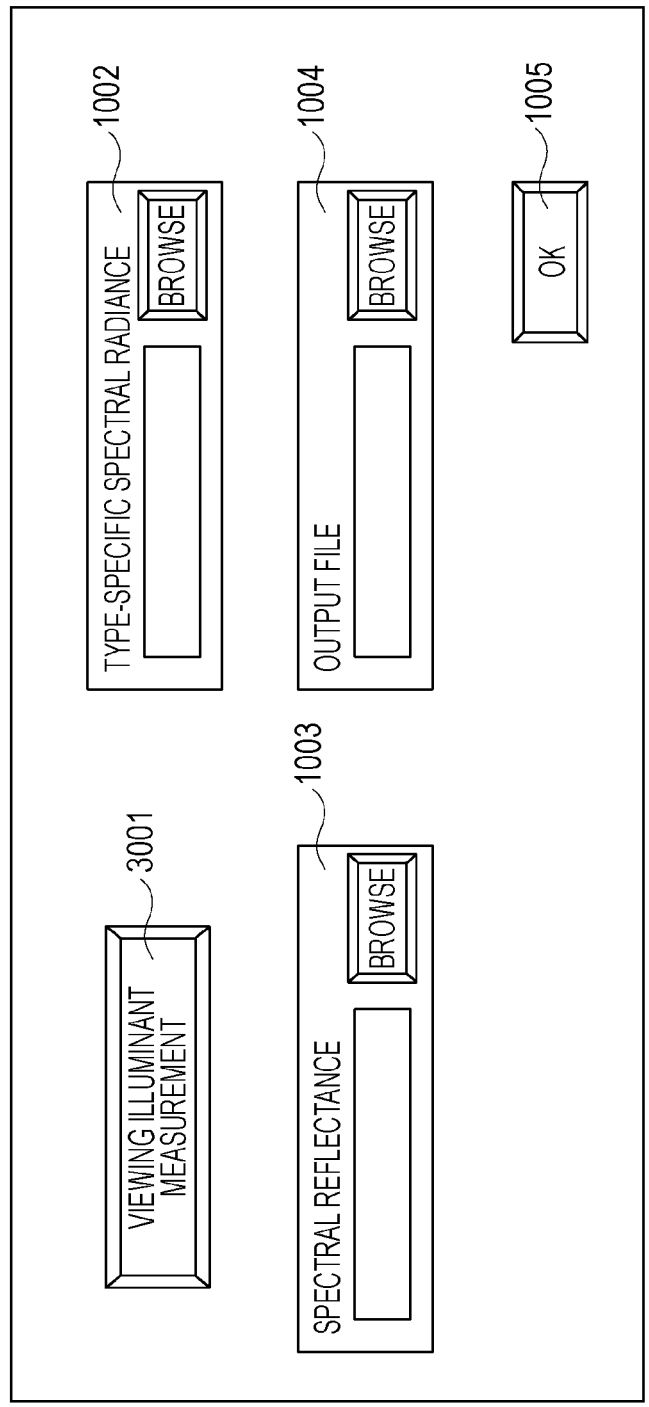
FIG. 15 illustrates a user interface according to the second embodiment.

FIG. 15 illustrates a user interface displayed in the second embodiment, in relation to the user interface displayed by the UI display unit 102 in step S1 of the first embodiment. Instead of the input section 1001 in the user interface example (see FIG. 5) of the first embodiment, a viewing illuminant measurement button 3001 is displayed in the user interface illustrated in FIG. 15. When the viewing illuminant measurement button 3001 is pressed by the user, the spectral-radiance input unit 303 issues an instruction to the external-device control unit 310 to control a colorimeter. Upon receipt of the instruction, the external-device control unit 310 controls the colorimeter (see FIG. 11) connected to the general-purpose interface 204 so as to measure the spectral radiance of the viewing illuminant. The measured spectral radiance of the viewing illuminant is input by the spectral-radiance input unit 303 as a data structure, such as that described in the first embodiment with reference to FIG. 6. The measurement data may be converted to the data structure either by the external-device control unit 310 or by the spectral-radiance input unit 303.

After the spectral radiance of the viewing illuminant is input as described above, the process described in the first embodiment can be performed.

As described above, according to the second embodiment, the colorimetric application connected to the colorimeter makes it possible to determine, with high accuracy, colors of a sample containing a fluorescent component under any viewing illuminant.

Third Embodiment

The above embodiments have described examples in which information is obtained from outside. A third embodiment describes an example of a configuration having a measuring function. For example, a colorimeter having a calculating function and a handheld computer having a colorimetric function are relevant to the present embodiment.

Figure 16:
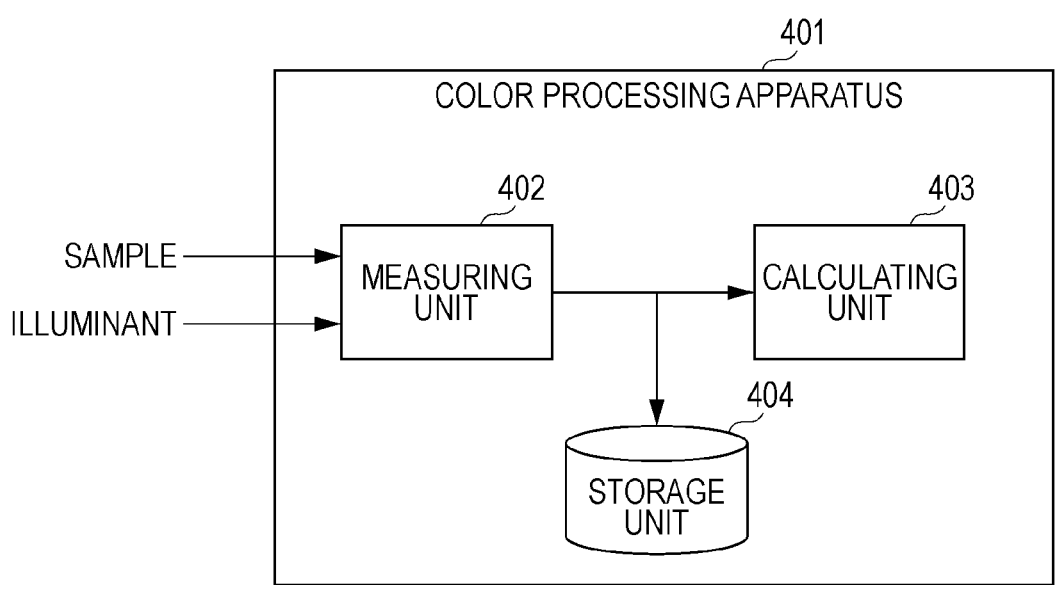
FIG. 16 illustrates a configuration of a color processing apparatus according to a third embodiment.
Figure 17:
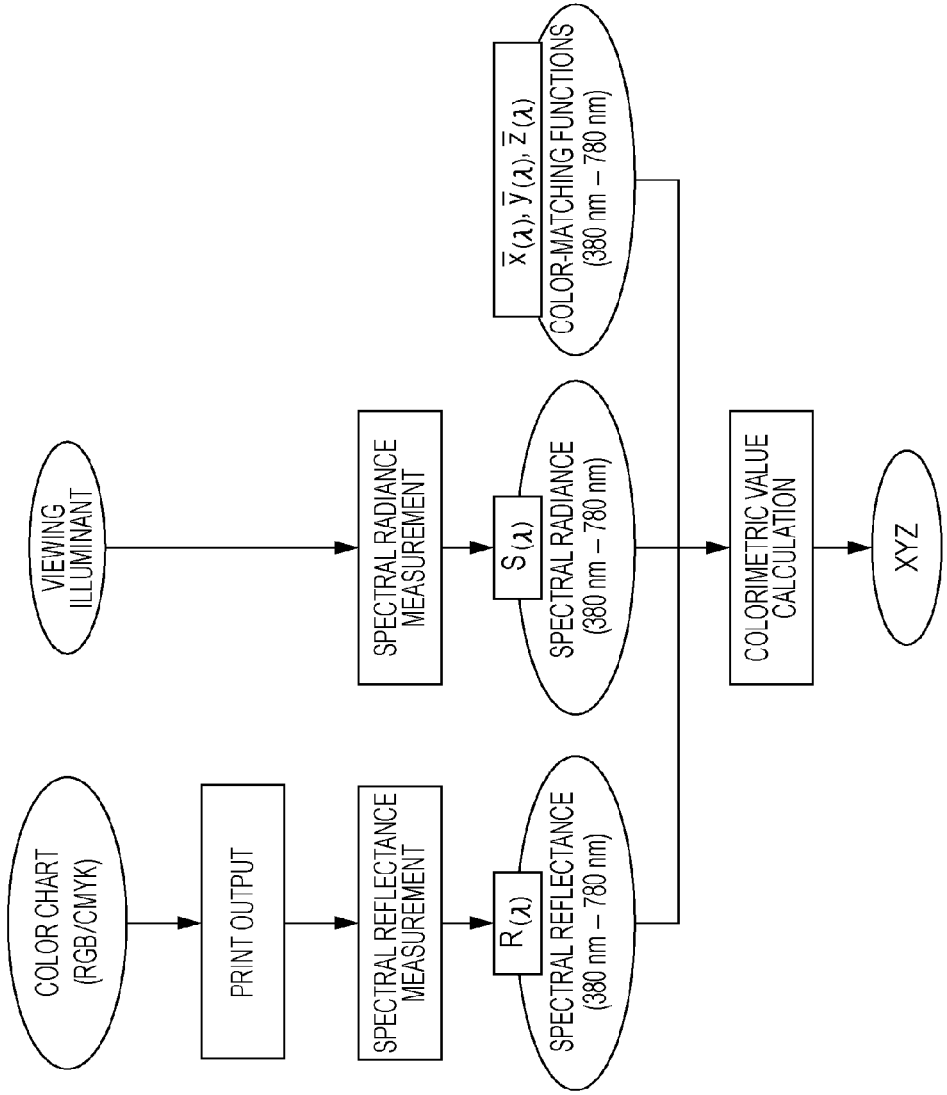
FIG. 17 illustrates a known example for calculating measurement values under a viewing illuminant.

FIG. 16 is a block diagram illustrating a configuration of a color processing apparatus according to the third embodiment. Referring to FIG. 16, a color processing apparatus 401 measures a color chart from an image output apparatus and a viewing illuminant, and calculates colorimetric values. The color processing apparatus 401 has the following configuration.

A measuring unit 402 measures illuminant information such as spectral radiance of a viewing environment including an excitation wavelength region; the amount of fluorescence in a sample, the amount corresponding to the spectral radiance of the viewing environment including the excitation wavelength region; and spectral reflectance of the sample.

The calculating unit 403 inputs the spectral reflectance of the sample and the spectral radiance of the illuminant that are measured in the measuring unit 402, and calculates the spectral reflectance of the sample corresponding to the viewing illuminant. The calculating unit 403 has a configuration which includes the spectral-radiance input unit 103, the waveform-type determining unit 104, the spectral-reflectance estimating unit 105, the colorimetric-value calculating unit 106, the type-specific spectral-radiance input unit 108, and the spectral-reflectance input unit 109 in the color processing apparatus 101 of the first embodiment.

A storage unit 404 stores the measurement values obtained in the measuring unit 402 and the results of calculation performed in the calculating unit 403. The measuring unit 402 includes illuminants of the different waveform types described in the first embodiment. The spectral radiance of the illuminant of each waveform type is stored in the storage unit 404. The measuring unit 402 measures spectral reflectance of the sample corresponding to the waveform type of each illuminant, and also measures spectral radiance of the viewing illuminant. The measuring unit 402 stores the measurement results in the storage unit 404. Each data stored in the storage unit 404 is input to the calculating unit 403 by the spectral-radiance input unit 103, the type-specific spectral-radiance input unit 108, and the spectral-reflectance input unit 109 that are included in the calculating unit 403, where colorimetric values of the sample corresponding to the viewing illuminant are calculated.

The color processing apparatus described in the third embodiment is configured such that spectral reflectance of a sample is measured under each of illuminants of different waveform types included in the color processing apparatus, spectral radiance of a viewing illuminant is measured, and the measurement data can be used by the calculating unit. Therefore, colors of a sample under any viewing illuminant can be determined with high accuracy by using the color processing apparatus alone.

Other Embodiments

In the embodiments described above, colorimetric values (XYZ values) of a sample corresponding to a viewing illuminant are output. However, the colorimetric values are not limited to this. For example, spectral reflectance of the sample may be directly output, or may be output after being converted to values in a perceptual space, such as CIELAB or CIECAM02.

Alternatively, a color profile created using such colorimetric values may be output. A color profile is a profile used in a color management system and in which color reproduction characteristics of a device are described. For example, in a typical color profile of an RGB printer, an LUT is described, which defines a correspondence between RGB and XYZ (CIELAB or CIECAM02) for a color chart of 729 (=9³) colors based on RGB, each having 9 steps. Therefore, it is possible to calculate XYZ of each color using the method described in the above embodiments, and create a color profile. In this case, spectral reflectance excluding fluorescence and the amount of fluorescence corresponding to each waveform type (see FIG. 9) are input for each color chart by the spectral-reflectance input unit 109 of the above embodiments. Then, the estimation of spectral reflectance in the spectral-reflectance estimating unit 105 and the calculation of colorimetric values in the colorimetric-value calculating unit 106 are performed for each color chart.

In the embodiments described above, the waveform-type determining unit 104 is configured to select one of three waveform types as a waveform type of a viewing illuminant. However, the waveform type of a viewing illuminant may not be limited to one type.

If the viewing illuminant is mixed light which is a mixture of a plurality of illuminants, it is possible to select a plurality of waveform types. For example, if an RMS error calculated by the waveform-type determining unit 104 between the viewing illuminant and each of waveform types is larger than a threshold value T, which is a predetermined value, the waveform types are combined together using the following equation (7). In the equation, s, t, and u are ratios of waveforms to be combined and s+t+u=1.

$$S'_{type\_i} = s \times S'_{type\_1} + t \times S'_{type\_2} + u \times S'_{type\_3} \qquad \text{equation (7)}$$

These ratios are repeatedly calculated until the RMS error from the viewing illuminant becomes less than or equal to the threshold value T. These ratios can also be used in calculating the amount of fluorescence in the spectral-reflectance estimating unit 105. Specifically, the amount of fluorescence can be calculated using the following equation (8).

$$F_v(\lambda) = (s \times F_{type\_1}(\lambda) + t \times F_{type\_2}(\lambda) + u \times F_{type\_3}(\lambda)) \times \text{ratio} \qquad \text{equation (8)}$$

In the embodiments described above, a waveform type of a viewing illuminant is determined on the basis of an RMS error from a plurality of waveform types. However, such a waveform type may be determined by specifying it through a user interface.

The process of calculating colorimetric values in the foregoing embodiments is applicable to a colorimeter that is integral with an image input device, a display device, or an output device. For example, in the case of a colorimeter integral with a printer, calculated colorimetric values can be used in calibrating the color reproduction characteristics of the printer and updating the color profile.

The present invention is also realized by performing the following process. In this process, computer-readable software (computer program) that realizes the functions of the foregoing embodiments is supplied to a system or an apparatus via a network or various storage media. Then, a computer (or CPU or MPU) of the system or apparatus reads and executes the program.

According to the present invention, it is possible to determine, with high accuracy, colors of a sample containing a fluorescent component under any viewing illuminant.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Application No. PCT/JP2009/068437, filed Oct. 27, 2009, which is hereby incorporated by reference herein in its entirety.

What is claimed is:

1. A color processing apparatus that calculates spectral reflectance including a fluorescent component in a sample under a target illuminant, the color processing apparatus comprising:
    first means for inputting, for each of a plurality of waveform types, spectral radiance including an excitation wavelength region and the amount of fluorescence in the sample corresponding to the spectral radiance;
    second means for determining, from spectral radiance of the target illuminant including the excitation wavelength region and the input spectral radiance and amount of fluorescence, the amount of fluorescence in the sample under the target illuminant;
    third means for inputting spectral reflectance excluding the fluorescent component in the sample; and
    fourth means for determining, by using the determined amount of fluorescence in the sample under the target illuminant and the input spectral reflectance excluding the fluorescent component in the sample, spectral reflectance including the fluorescent component in the sample under the target illuminant.

2. The color processing apparatus according to claim 1, wherein the plurality of waveform types are a plurality of waveforms classified into typical shapes.

3. The color processing apparatus according to claim 1, wherein the excitation wavelength region is an excitation wavelength region of a fluorescent whitener applied to the sample, and includes at least a wavelength region from 300 nm to 500 nm.

4. The color processing apparatus according to claim 1, wherein the second means includes
    determining means for comparing the spectral radiance of the target illuminant including the excitation wavelength region to the input spectral radiance for each of the plurality of waveform types, and determining a waveform type for the spectral radiance of the target illuminant including the excitation wavelength region;
    calculating means for determining a ratio between the spectral radiance of the target illuminant including the excitation wavelength region and the spectral radiance for the determined waveform type; and
    obtaining means for obtaining the amount of fluorescence in the sample under the target illuminant by multiplying the amount of fluorescence for the determined waveform type by the ratio.

5. The color processing apparatus according to claim 2, wherein the second means includes
    determining means for comparing the spectral radiance of the target illuminant including the excitation wavelength region to the input spectral radiance for each of the plurality of waveform types, and determining a waveform type for the spectral radiance of the target illuminant including the excitation wavelength region;
    calculating means for determining a ratio between the spectral radiance of the target illuminant including the excitation wavelength region and the spectral radiance for the determined waveform type; and
    obtaining means for obtaining the amount of fluorescence in the sample under the target illuminant by multiplying the amount of fluorescence for the determined waveform type by the ratio.

6. The color processing apparatus according to claim 3, wherein the second means includes determining means for comparing the spectral radiance of the target illuminant including the excitation wavelength region to the input spectral radiance for each of the plurality of waveform types, and determining a waveform type for the spectral radiance of the target illuminant including the excitation wavelength region;

calculating means for determining a ratio between the spectral radiance of the target illuminant including the excitation wavelength region and the spectral radiance for the determined waveform type; and obtaining means for obtaining the amount of fluorescence in the sample under the target illuminant by multiplying the amount of fluorescence for the determined waveform type by the ratio.

7. The color processing apparatus according to claim 4, wherein the determining means determines, as a waveform type of the target illuminant, a waveform type for which an RMS error between the spectral radiance of the target illuminant in the excitation wavelength region and the spectral radiance for the waveform type in the excitation wavelength region is the smallest of those for the plurality of waveform types.

8. The color processing apparatus according to claim 5, wherein the determining means determines, as a waveform type of the target illuminant, a waveform type for which an RMS error between the spectral radiance of the target illuminant in the excitation wavelength region and the spectral radiance for the waveform type in the excitation wavelength region is the smallest of those for the plurality of waveform types.

9. The color processing apparatus according to claim 6, wherein the determining means determines, as a waveform type of the target illuminant, a waveform type for which an RMS error between the spectral radiance of the target illuminant in the excitation wavelength region and the spectral radiance for the waveform type in the excitation wavelength region is the smallest of those for the plurality of waveform types.

10. The color processing apparatus according to claim 4, wherein if an RMS error between the spectral radiance of the target illuminant in the excitation wavelength region and the spectral radiance for the waveform type in the excitation wavelength region is larger than a predetermined value, the determining means determines a waveform type that can be obtained by combining spectral radiances for the plurality of waveform types in the excitation wavelength region as a waveform type of the target illuminant.

11. The color processing apparatus according to claim 5, wherein if an RMS error between the spectral radiance of the target illuminant in the excitation wavelength region and the spectral radiance for the waveform type in the excitation wavelength region is larger than a predetermined value, the determining means determines a waveform type that can be obtained by combining spectral radiances for the plurality of waveform types in the excitation wavelength region as a waveform type of the target illuminant.

12. The color processing apparatus according to claim 6, wherein if an RMS error between the spectral radiance of the target illuminant in the excitation wavelength region and the spectral radiance for the waveform type in the excitation wavelength region is larger than a predetermined value, the determining means determines a waveform type that can be obtained by combining spectral radiances for the plurality of waveform types in the excitation wavelength region as a waveform type of the target illuminant.

13. The color processing apparatus according to claim 4, wherein the obtaining means obtains fluorescence in the sample under the target illuminant, the fluorescence being obtained by multiplying the amount of fluorescence for the determined waveform type in a visible wavelength region by the ratio.

14. The color processing apparatus according to claim 5, wherein the obtaining means obtains fluorescence in the sample under the target illuminant, the fluorescence being obtained by multiplying the amount of fluorescence for the determined waveform type in a visible wavelength region by the ratio.

15. The color processing apparatus according to claim 6, wherein the obtaining means obtains fluorescence in the sample under the target illuminant, the fluorescence being obtained by multiplying the amount of fluorescence for the determined waveform type in a visible wavelength region by the ratio.

16. The color processing apparatus according to claim 1, wherein the fourth means adds the determined amount of fluorescence in the sample under the target illuminant to the input spectral reflectance excluding the fluorescent component in the sample to determine the spectral reflectance including the fluorescent component in the sample under the target illuminant.

17. The color processing apparatus according to claim 1, further comprising measuring means for measuring spectral radiance including the excitation wavelength region and the amount of fluorescence in the sample corresponding to the spectral radiance, wherein the first means inputs the spectral radiance including the excitation wavelength region and the amount of fluorescence in the sample corresponding to the spectral radiance, the spectral radiance and the amount of fluorescence being measured by the measuring means.

18. A color processing method for calculating spectral reflectance including a fluorescent component in a sample under a target illuminant, the color processing method comprising:
a first step of inputting, for each of a plurality of waveform types, spectral radiance including an excitation wavelength region and the amount of fluorescence in the sample corresponding to the spectral radiance;
a second step of determining, from spectral radiance of the target illuminant including the excitation wavelength region and the input spectral radiance and amount of fluorescence, the amount of fluorescence in the sample under the target illuminant;
a third step of inputting spectral reflectance excluding the fluorescent component in the sample; and
a fourth step of determining, by using the determined amount of fluorescence in the sample under the target illuminant and the input spectral reflectance excluding the fluorescent component in the sample, spectral reflectance including the fluorescent component in the sample under the target illuminant.

19. A computer-readable storage medium that stores a program for causing a computer, by being executed by the computer, to function as each means of the color processing apparatus according to claim 1.

* * * * *